United States Patent
Nirwing et al.

(10) Patent No.: US 8,608,251 B2
(45) Date of Patent: Dec. 17, 2013

(54) BRUSH HEAD MANUFACTURING METHOD

(75) Inventors: Raimund Nirwing, Limburg (DE); Frank Gliemroth, Schwalbach (DE); Ulrich Stoerkel, Bad Nauheim (DE); Thomas Fritsch, Eppstein (DE)

(73) Assignee: Braun GmbH, Kronberg (DE)

( * ) Notice: Subject to any disclaimer, the term of this patent is extended or adjusted under 35 U.S.C. 154(b) by 240 days.

(21) Appl. No.: 13/236,903

(22) Filed: Sep. 20, 2011

(65) Prior Publication Data
US 2012/0073070 A1 Mar. 29, 2012

(30) Foreign Application Priority Data

Sep. 29, 2010 (EP) .................................... 10011394

(51) Int. Cl.
*A46D 3/00* (2006.01)
(52) U.S. Cl.
USPC .......................................................... 300/21
(58) Field of Classification Search
USPC .......................................................... 300/21
See application file for complete search history.

(56) References Cited

U.S. PATENT DOCUMENTS

| | | | |
|---|---|---|---|
| 4,892,698 A * | 1/1990 | Weihrauch | 264/243 |
| 5,129,191 A * | 7/1992 | Warner et al. | 451/466 |
| 5,778,474 A | 7/1998 | Shek | |
| 6,406,099 B2 * | 6/2002 | Boucherie | 300/21 |
| 6,892,412 B2 | 5/2005 | Gatzemeyer et al. | |
| 7,430,778 B2 | 10/2008 | Gatzemeyer et al. | |
| 2003/0140435 A1 | 7/2003 | Eliav et al. | |
| 2003/0140437 A1 | 7/2003 | Eliav et al. | |
| 2005/0000043 A1 | 1/2005 | Chan et al. | |
| 2008/0313830 A1 | 12/2008 | Gatzemeyer et al. | |
| 2009/0183324 A1 | 7/2009 | Fischer et al. | |

FOREIGN PATENT DOCUMENTS

DE  35 44 256 A1  6/1987

OTHER PUBLICATIONS

PCT International Search Report dated Jun. 24, 2008.

* cited by examiner

*Primary Examiner* — Mark Spisich
(74) *Attorney, Agent, or Firm* — John P. Colbert

(57) ABSTRACT

A method of manufacturing a brush head is disclosed. The method includes the steps of providing a bristle carrier on which at least a bristle tuft including a plurality of bristles is mounted; providing a cover structure having at least an aperture; constraining the free ends of the plurality of bristles of the bristle tuft into a defined cross sectional geometry such that it fits within the cross sectional area of the aperture; moving the cover structure and the bristle carrier relative to each other until the constrained bristle tuft and the aperture are positioned in spatial alignment; and releasing the constraint while moving the cover structure into a destination position in which the bristle tuft extends through the aperture.

12 Claims, 5 Drawing Sheets

BRUSH HEAD MANUFACTURING METHOD

CROSS REFERENCE TO RELATED APPLICATIONS

This application claims the benefit of European Patent Convention Application No. 10011394.3, filed Sep. 29, 2010, the substance of which is incorporated by reference in its entirety herein.

FIELD OF THE INVENTION

The present disclosure is directed to a manufacturing method of a brush head for a toothbrush. More particularly, the present disclosure is directed to a brush head for a toothbrush.

BACKGROUND OF THE INVENTION

It is known that a brush head for a toothbrush can be manufactured by providing a carrier on which one or several bristle tufts each comprising a plurality of bristles is mounted (for example, using anchor tufting technology). The carrier may then be mounted to a brush tube so as to be moveable relative to the brush tube; for example, the carrier may be a disk that is mounted to a brush tube for rotary oscillation around an axis being perpendicular to the longitudinal extension axis of the brush tube (for example, as is known from the Precision Clean brush head from Oral-B).

It is a desire to provide a manufacturing method for a brush head that provides for further design options.

SUMMARY OF THE INVENTION

In one embodiment, a method of manufacturing a brush head is provided. The method includes the steps of providing a bristle carrier on which at least a bristle tuft including a plurality of bristles is mounted; providing a cover structure having at least an aperture; constraining the free ends of the plurality of bristles of the bristle tuft into a defined cross sectional geometry such that it fits within the cross sectional area of the aperture; moving the cover structure and the bristle carrier relative to each other until the constrained bristle tuft and the aperture are positioned in spatial alignment; and releasing the constraint while moving the cover structure into a destination position in which the bristle tuft extends through the aperture.

In another embodiment, a brush head is provided. The brush head includes a cover structure having at least an aperture and a bristle carrier on which at least a bristle tuft having a plurality of bristles is mounted, which bristle tuft extends through the aperture. The aperture has in at least a first spatial aperture extension direction a smaller width than the respective width of the bristle tuft at its free end.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
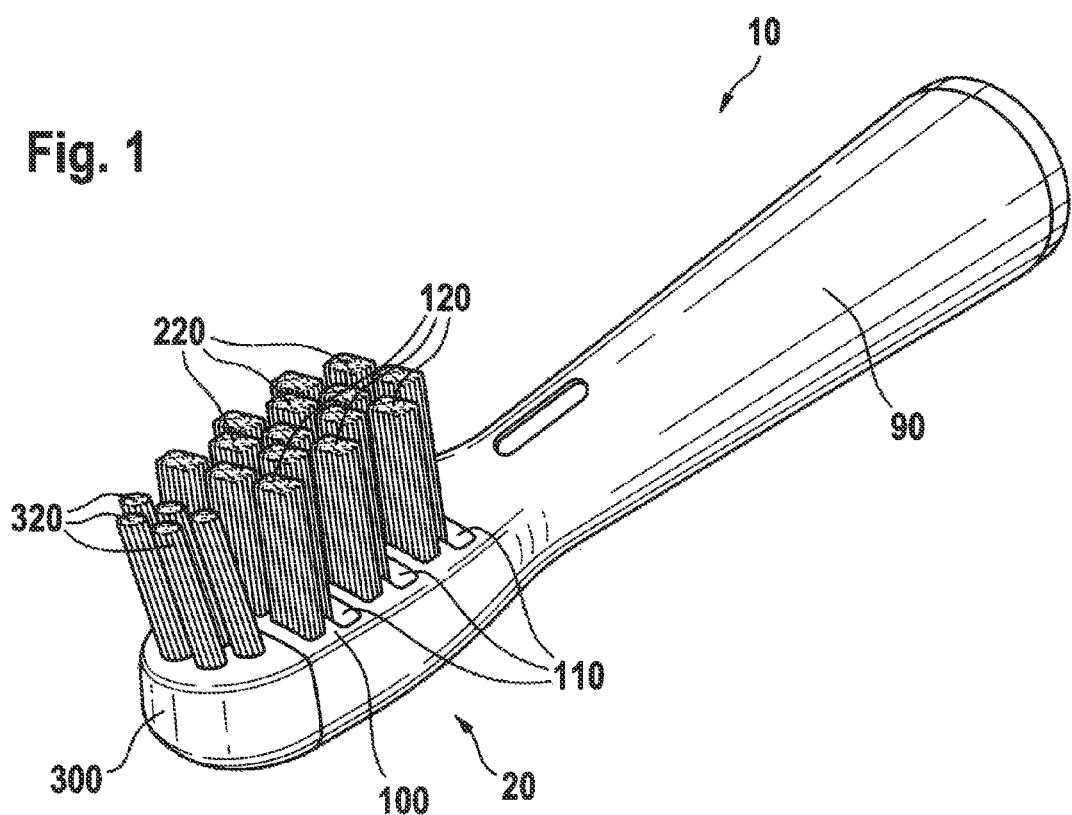
FIG. 1 is a depiction of an exemplary brush head according to embodiments shown and described herein.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

In accordance with the present disclosure, a method of manufacturing a brush head is proposed that includes the steps of:

providing a bristle carrier on which at least a bristle tuft comprising a plurality of bristles is mounted and a cover structure having at least an aperture;

constraining the free ends of the plurality of bristles of the bristle tuft into a defined cross sectional geometry such that it fits within the cross sectional area of the aperture;

moving the cover structure and the bristle carrier relative to each other until the constrained bristle tuft and the aperture are positioned in spatial alignment; and releasing the constraint while moving the cover structure into a destination position in which the bristle tuft extends through the aperture.

Here, "constraining" of a bristle tuft essentially means at least bringing the bristle tuft into a predefined cross sectional shape and in particular decreasing a cross sectional area of the bristle tuft by reducing the average distance between the bristles of the bristle tuft.

By using the method described herein, bristle tufts that have a width in a first spatial extension direction of their free ends that is about as large or even larger than the respective width of the aperture can be slid into the aperture while any damages (i.e. jammed bristles, broken bristles etc.) that may occur otherwise are effectively avoided.

In one embodiment, a constraining structure is used to constrain the bristle tuft. The constraining structure may have two or more constraining elements. At least one constraining element may have a comb-like structure. The prongs of this comb-like structure may have rounded edges. The present disclosure is also concerned with a toothbrush that comprises a brush head made in accordance with the proposed manufacturing method.

In another embodiment, a brush head having a cover structure having at least an aperture and a bristle carrier on which at least a bristle tuft comprising a plurality of bristles is mounted, which bristle tuft extends through the aperture, wherein the aperture has in at least a first spatial aperture extension direction a smaller width than the respective width of the bristle tuft at its free end and a toothbrush comprising such a brush head are provided.

Figure 7:
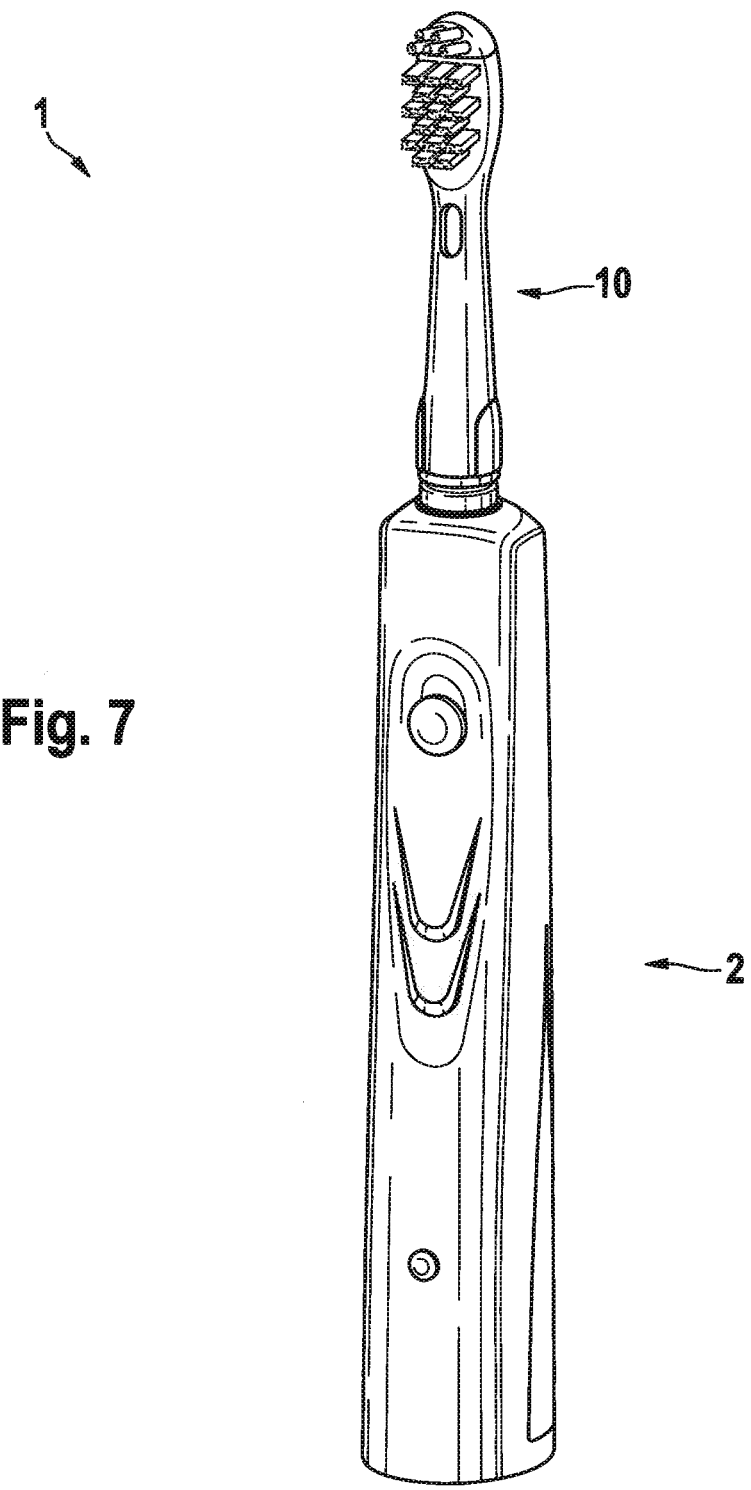
FIG. 7 is a depiction of an exemplary toothbrush having a brush head according to embodiments shown and described herein.

FIG. 1 shows an exemplary brush head 10 as proposed, which, in one embodiment, is a replaceable brush head that is intended for use with a handle 2 of an electric toothbrush 1 as shown in FIG. 7. In one embodiment, the brush head 10 has a tubular neck section 90 and a head section 20. The head section 20 includes a cover structure 100 having apertures 110 that are elongated in a direction perpendicular to the longitudinal extension direction of the brush head 10. In this exemplary embodiment, two bristle tufts 220 extend through each of the apertures 110, respectively. As will be explained in more detail with reference to FIG. 2, the bristle tufts 220 are mounted on a bristle carrier, which in the shown exemplary embodiment may be arranged for driven movement, in particular an oscillatory rotational motion around an axis that is essentially parallel to the longitudinal extension axis of the brush head 10. Further cleaning elements 120, which are here realized as further bristle tufts, are mounted on the cover structure 100 such that the overall field of bristle tufts comprises alternately arranged rows of bristle tufts mounted on the cover structure 100 and on the bristle carrier. In addition, the brush head 10 as shown has a front part 300 on which further cleaning elements 320 are mounted. Instead of being realized as bristle tufts, at least some of the cleaning elements 120, 220 or 320 mounted on the cover structure 100, on the bristle carrier or on the front part 300 could also be realized as, for example, elastomeric fingers or the like.

Figure 2:
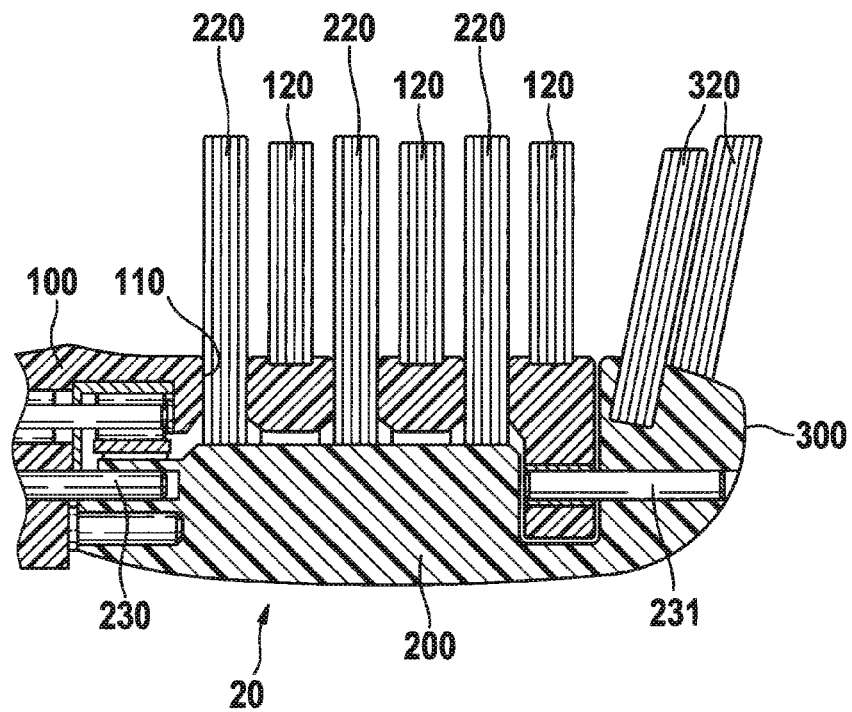
FIG. 2 is a cross sectional cut through the head section of the brush head shown in FIG. 1.

FIG. 2 is a cross sectional cut through the head section 20 of the brush head 10 shown in FIG. 1. Here, it can be seen that a bristle carrier 200 may be arranged underneath the cover structure 100. The bristle carrier 200 extends from a first end of the head section 20 that is proximal the tubular neck section 90 to a second end forming the front part 300 of the brush head. In one embodiment, the bristle carrier 200 is mounted via mounting pins 230, 231 at the cover structure 100 so that the bristle carrier 200 can be driven into an oscillatory rotation around the axis defined by the mounting pins 230 and 231. Bristle tufts 220 that are mounted on the bristle carrier 200 extend through apertures 110 provided in the cover structure 100. As will be further explained with reference to FIG. 3A and FIG. 4, the width of the aperture 110 in the longitudinal aperture extension direction of the brush head is only slightly larger than the width of the bristle tuft 220, for example, the width of the bristle tuft close to the mounting surface in longitudinal aperture extension direction may be in the order of about 0.5 mm to about 4 mm and the respective width of the aperture may then be only about 0.1 mm larger. The width of the aperture 110 in the lateral aperture extension direction perpendicular to the longitudinal aperture extension direction is wider than the width of the two bristle tufts 220 arranged in a row to enable the wiping motion of the bristle tufts 220 mounted on the bristle carrier 200. Further cleaning elements 120 are mounted to the cover structure 100. The longitudinal aperture extension direction and the lateral aperture extension direction are two spatial aperture extension directions and generally, the aperture has at least a first spatial aperture extension direction in which the aperture is smaller than the width of the respective bristle tuft extending through the aperture at its free end, in particular, the width of the free end of the bristle tuft in a state at which it is mounted to the bristle carrier 200 but does not extend through the aperture. Below, it will be explained how it can be achieved that the bristle tuft 220 is slid into the aperture with effectively avoiding the risk of bending, breaking etc. any bristles of the bristle tuft.

Figure 3A:
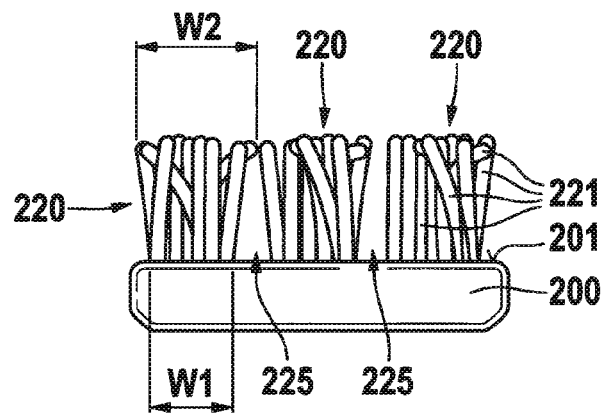
FIG. 3A is a schematic side view of a bristle carrier having bristle tufts mounted to a mounting surface of the bristle carrier.

FIG. 3A is a schematic depiction of a bristle carrier 200 having a mounting surface 201 on which bristle tufts 220 (here: three bristle tufts 220) are mounted (the technology of mounting bristle tufts is generally known in the art, for example, tufting holes may be provided in the bristle carrier into which bristle bunches are mounted using stapling technology; other technologies like in-mold technology or AFT—anchor free tufting—may also be used). Each bristle tuft 220 comprises a plurality of bristles 221 (a bristle 221 may be a filament made from polyamide, for example, nylon-6.6, and may have a diameter lying in the range of about 100 micrometers to about 200 micrometers). The bristle tufts 220 are separated by gaps 225, where due to the angled extension of the bristles 221, the gaps 225 between the bristle tufts 220 narrow towards the free ends of the bristle tufts 220 or may even vanish as the bristles 221 of different tufts may intermingle at the free ends. In general, the exemplary manufacturing method does not require several bristle tufts to be mounted to a bristle carrier, hence there may be only a single bristle tuft mounted to the bristle carrier, or there may be two bristle tufts or there may be three, four, five etc. bristle tufts mounted to the bristle carrier. The bristle tufts may be mounted in a rather random manner or they may be mounded in a regular manner, for example, in a row or several rows (for example, a bristle carrier may have two rows of bristle tufts, each row comprising two bristle tufts each). It is indicated in FIG. 3A that the width W1 of a bristle tuft 220 in a given spatial extension direction at the level of the mounting surface 201 is smaller than the width W2 of the same bristle tuft 220 at its upper free end as the bristle tufts 220 usually widen towards the free ends of the bristles 221 caused by the bristles 221 not extending in parallel to each other but under a certain angle (similar to a bunch of cut flowers).

Figure 3B:
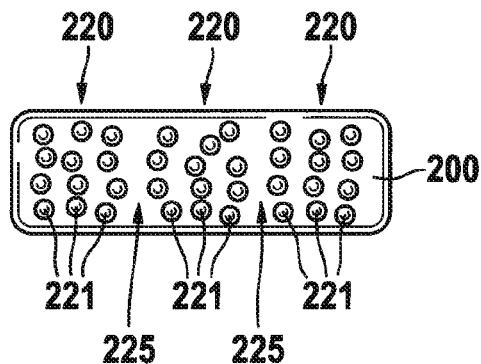
FIG. 3B is a schematic top view onto the bristle carrier shown in FIG. 3A.

FIG. 3B is a top view onto the schematically depicted bristle carrier 200 shown in FIG. 3A. Each bristle tuft 220 mounted at the bristle carrier 200 includes a plurality of bristles 221. The tufts are separated by gaps 225. It is here indicated that in each bristle tuft 220—even though they may have the same number of bristles 221—the bristle pattern (position of bristles) may be (slightly) different and further the density of the bristles 221 in a bristle tuft 220 is less than the highest possible packaging density (and the density may be different from bristle tuft to bristle tuft). The highest possible packaging density of cylinders of equal diameter is 91%, while the packaging density of the bristles in a bristle tuft (at the level of the mounting surface) may be in the order of about 50% to about 80% and may in particular be about 60% or about 70%. In FIG. 3B it is—for sake of clarity—essentially neglected that the bristles extend with different angles to each other instead of parallel to each other.

Figure 4:
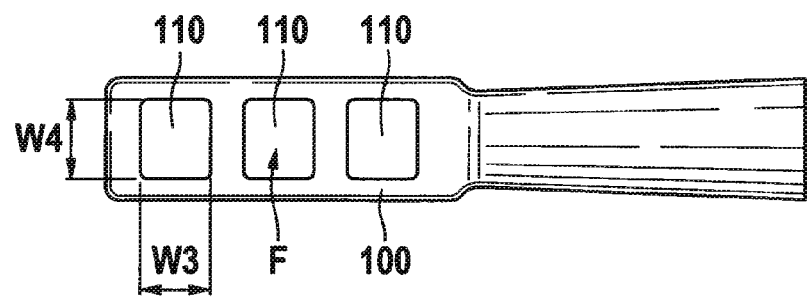
FIG. 4 is a schematic top view onto a cover structure intended for being mounted on top of the bristle carrier shown in FIGS. 3A and 3B such that the bristle tufts extend through apertures of the cover structure.

FIG. 4 is a schematic depiction of a cover structure 100 having apertures 110. In the shown embodiment, the cover structure 100 has three apertures 110 coinciding with the number of bristle tufts of the bristle carrier shown in FIGS. 3A and 3B. As was stated for the number of bristle tufts mounted to the bristle carrier 200 above, it is—without loss of generality, i.e. without losing the general underlying concept of the exemplary manufacturing method—also sufficient that the cover structure has a single aperture, but the cover structure may also have more than one aperture, it may have two, three, four, five etc. apertures. The apertures may be arranged randomly or in a regular pattern, but as it is intended that bristle tufts mounted on a bristle carrier shall extend through the apertures in a mounted state of the brush head, the respective bristle tufts and the apertures are arranged in a spatially coinciding manner. This does not necessarily require that the number of apertures is identical to the number of bristle tufts as two or more bristle tuft may finally extend through a single aperture (an example was discussed with reference to FIG. 1). It shall also not be excluded that further apertures may be present through which, for example, other cleaning elements may extend in the mounted state of the brush head. Further, it shall also not be excluded that one or several further cleaning elements, in particular bristle tufts, are mounted on the bristle carrier, which will finally not extend through any of the apertures. The width of an aperture 110 in a first spatial aperture extension direction is W3 (here: the longitudinal aperture extension direction) and the width of the aperture in a second spatial aperture extension direction is W4 (here: the lateral aperture extension direction). In case the width W3 is about as large as or only slightly larger than the corresponding width W1 of a bristle tuft 220 (as indicated in FIG. 3A) but is also smaller than the width W2 of the bristle tuft at its free end, than it is obvious that the cover structure 100 cannot simply be slid over the bristle tufts 220 until the bristle tufts 220 extend through the apertures 110, as one or several bristles 221 of the bristle tufts 220 that extend into the area that lies beyond the width W3 of the aperture 110 may get bent and eventually damaged or broken such that a single or several bristles 221 may finally not extend through the aperture 110, but may in particular be jammed between the cover structure and the bristle carrier. Each aperture 110 has a cross sectional area F, which in the shown embodiment is identical for the three apertures 110. In general, each aperture may have a different cross sectional area F (in particular, the widths W3 and W4 may differ between the apertures, but also the geometry of the cross sectional areas may vary in many aspects, for example, the shape of the cross sectional areas may not be essentially rectangular as shown here but may be triangular, circular, oval, or it may be irregular). Similarly, the bristle tufts may have different cross sectional shapes.

An exemplary manufacturing method for a brush head is now discussed with reference to FIGS. 5A-5C and FIGS. 6A-6D that effectively avoids bent, damaged, broken or jammed bristles.

Figure 5A:
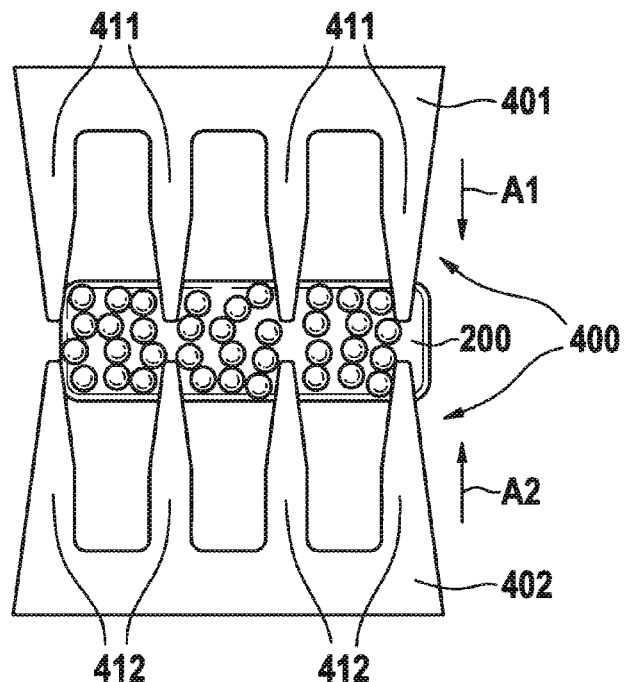
FIG. 5A is a schematic depiction of an intermediate step of an exemplary manufacturing method in which constraining elements forming a constraining structure are moved in between the bristle tufts.

FIG. 5A is a schematic depiction of a first stage of the manufacturing method. A bristle carrier 200 as shown in FIG. 3B to which three exemplary bristle tufts 220 are mounted is provided. The bristle carrier 200 may in particular be held by a machine at a precise location. A constraining structure 400 is provided, that here comprises two constraining elements 401 and 402 that are each arranged as comb-like constraining elements having prongs 411 and 412, respectively. In this step of the manufacturing method, the first comb-like constraining element 401 is moved relatively towards the bristle carrier 200 in the direction indicated by arrow A1 and the second comb-like constraining element 402 is relatively moved towards the bristle carrier 200 along the direction indicated by arrow A2. It is generally to be noted that movements between two objects described in the present application can be implemented by moving only one of the objects or both objects, for example, here the first comb-like constraining element 401 could be moved while the bristle carrier 200 is held stationary, the bristle carrier 200 can be moved while the first comb-like constraining element 401 is held stationary or the bristle carrier 200 and the first comb-like constraining element 401 may both be moved, for example, simultaneously or successively. Here, the first comb-like constraining element 401 can be moved into direction A1 first and then the second comb-like constraining element 402 can be moved in direction A2 or both constraining elements 401, 402 can be moved simultaneously. When the comb-like constraining elements 401, 402 are moved, the prongs 411 and 412 move in between the bristle tufts 220 (i.e. the prongs 411, 412 move into the gaps 225 indicated in FIGS. 3A and 3B), thereby separating the bristles of the respective bristle tufts into bunches that relate to an individual bristle tuft. The prongs 411 and 412 are here tapered towards their free ends and the prongs 411 and 412 may have in particular rounded edges so that damage to the bristles is effectively avoided. Due to the tapering of the prongs 411 and 412, the bristles of the bristle tufts 220 are first separated and then constrained into a higher bristle packaging density, as will become clear from FIG. 5B.

Figure 5B:
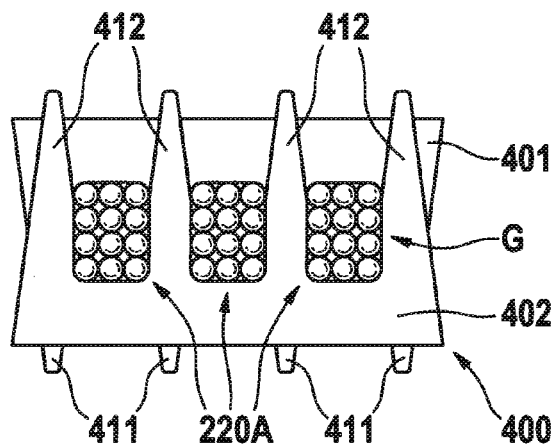
FIG. 5B is a schematic depiction of an intermediate step of the exemplary manufacturing method in which the constraining elements are in a desired end position in which the bristle tufts are constrained into a predefined geometry.

FIG. 5B is the same top view as in FIG. 5A but with the two constraining elements 401 and 402 of the constraining structure 400 being in a final constraining position. In this final constraining position, the remaining gaps between the comb-like constraining elements 401 and 402 define the cross sectional area G of the constrained bristle tufts 220A, where in the shown embodiment, the cross sectional area G is essentially rectangular and identical for the three constrained bristle tufts 220A. Even though the exemplary embodiment as shown has three cross sectional areas G of identical form, it shall again not be excluded that each of the cross sectional areas may have a different shape and/or size, where in particular the shape may deviate from the shape of the bristle tuft itself. It is understood that the spatial positions and the individual cross sectional areas G are chosen such that they on one hand coincide with the spatial position of the apertures and on the other hand fit within the cross sectional areas F of the apertures, respectively. While the bristle packaging density in the unconstrained bristle tuft may be, for example, about 70%, as was explained above, the bristle packaging density in the constrained bristle tuft may be higher, for example, about 85%. The constraining of the bristle tufts may increase the bristle packaging density by an absolute bristle packaging density value of for example, about 5%, 10%, 15%, 20%, 25%, 30%, or 35% (i.e. if an original bristle packaging density of 70% is increased by 5%, the bristle packaging density in the constrained bristle tuft is 75%), where of course a bristle packaging density of about 91% defines the upper limit (where this theoretical value is of course only valid for perfect cylinders of identical diameter, and the actual upper limit of the bristle packaging density depends in particular on the cross sectional geometry of the individual bristles in a bristle tuft). The cross sectional geometry of the constraint bristle tufts 220A may in particular be chosen such that the bristles are not damaged or deformed by the constraining process, hence a bristle packaging density of 75%, 76%, 77%, 78%, 79%, 80%, 81%, 82%, 83%, 84%, 86%, 87%, 88%, 89%, or 90% may be chosen as the upper limit for the to be achieved bristle packaging density when assuming that the bristles can be approximated as ideal cylinders.

In a case where a two-dimensional separation of bristle tufts is needed, an additional second constraining structure that also may comprises two constraining elements may be provided and may, for example, be moved along a direction being angled to the direction the first constraining structure is moved (in particular: this angled direction may be essentially perpendicular to the direction into which the first constraining structure is moved), so that finally a two-dimensional pattern of constrained bristle tufts results. In such an embodiment, the first and second constraining structures that may be considered as sub-constraining structures form together the constraining structure in accordance with the exemplary manufacturing method.

Figure 5C:
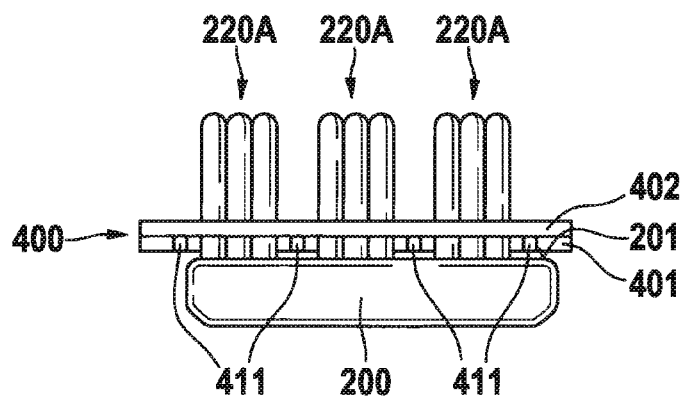
FIG. 5C is a side view onto the embodiment as shown in FIG. 5B.

FIG. 5C is a side view of the situation as schematically shown in FIG. 5B. It can in particular be seen that the prongs of the constraining elements of the constraining structure 400 were moved in between the bristle tufts close to the mounting surface 201 of the bristle carrier 200. The separation between the bristle tufts is ideal at the level of the mounting surface, where the bristle tufts are essentially constrained by, for example, the size and geometry of their tufting holes in case the bristle tufts were mounted using stapling technology (anchor tufting). The bristle tufts widen towards their free ends as had been explained before. Hence, it may not be reliable to slide in the constraining elements at a certain distance to the mounting surface 201 (for example, closer to the free ends of the bristle tufts than to the mounting surface) as then individual bristles from neighboring bristle tufts may get confined together with the bristles of the respective constrained bristle tuft. In a scenario where there is enough distance between the tufts so that the bristles of individual bristle tufts do not get intermingled with each other there may be no specific necessity to move the constraining elements close to the mounting surface.

It is to be noted that other geometries of the constraining elements of the constraining structure are also possible. For example, in one further embodiment, the first constraining element may be a comb-like constraining element as shown in FIGS. 5A and 5B, while the second constraining element may be a counter plate having recesses or holes into which the tips of the prongs may extend in the final position as shown in FIG. 5B.

Figure 6A:
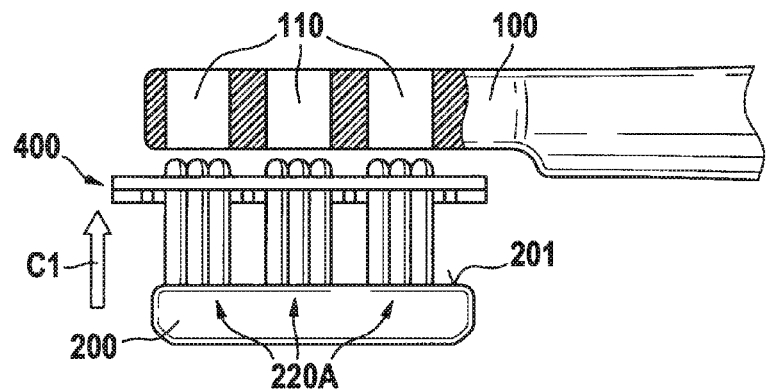
FIG. 6A is a schematic depiction of an intermediate step of an exemplary manufacturing method in which the constraining structure is moved upwards towards the free ends of the constrained bristle tufts and a cover structure is moved into a position assuring spatial alignment of the apertures and the free ends of the constrained bristle tufts.

In FIG. 6A an intermediate step of the exemplary manufacturing method is schematically depicted in which the cover structure 100 is already disposed near the bristle carrier 200, where the apertures 110 are already in spatial alignment with the position of the free ends of the constrained bristle tufts 220A. In contrast to the situation shown in FIG. 5C, the constraining structure 400 is moved away from the mounting surface 201 of the bristle carrier 200 towards the free ends of the constrained bristle tufts 220A, as indicated by arrow C1, whereby the constrained bristle tufts 220A get forced into the constrained geometry at their free ends and any unwanted widening of the bristle tufts towards their free ends is essentially avoided.

Figure 6B:
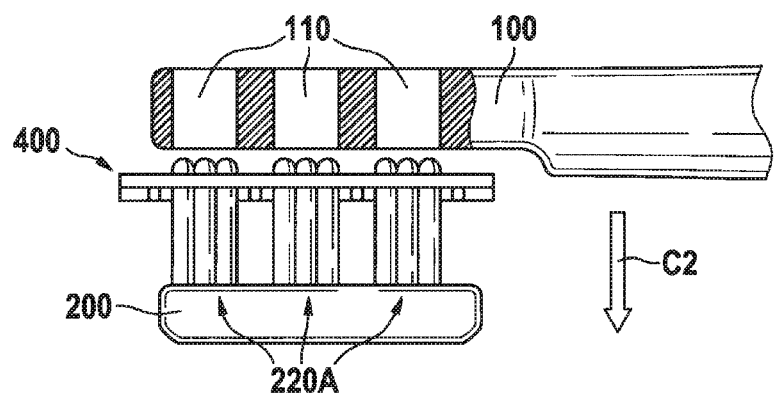
FIG. 6B shows the is a schematic depiction of an intermediate step of an exemplary manufacturing method in which the cover structure is moved towards the bristle carrier.

In FIG. 6B the next step of the exemplary manufacturing method is indicated, in which the cover structure 100 is moved towards the free ends of the constrained bristle tufts 220A in a direction C2. As the apertures 110 and the free ends of the constrained bristle tufts 220A were already in spatial alignment and as the free ends of the constrained bristle tufts 220A are each individually confined into a geometry G (as was explained with reference to FIG. 5B) that fits within the geometry F (as indicated in FIG. 4) of the respective aperture 110 through which the respective bristle tuft shall finally extend, the free ends of the constrained bristle tufts 220A will easily glide into the apertures 110 without bending or breaking any of the individual bristles.

Figure 6C:
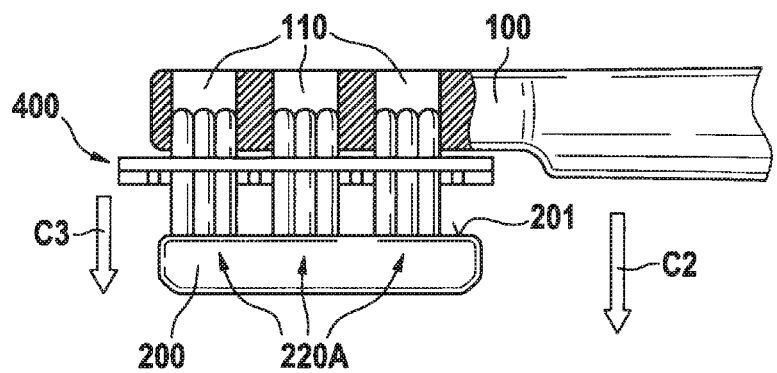
FIG. 6C is a schematic depiction of an intermediate step of an exemplary manufacturing method in which the constrained bristle tufts extend into the apertures and the constraining structure is move simultaneously with the cover layer.
Figure 6D:
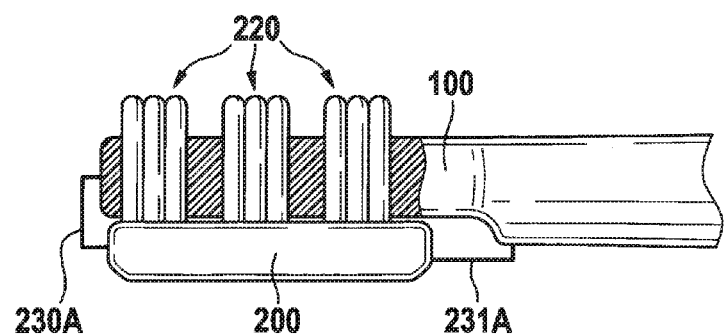
FIG. 6D is a schematic depiction of an intermediate step of an exemplary manufacturing method in which the bristle tufts fully extend through the apertures and the bristle carrier and the cover structure are mounted each other.

In FIG. 6C a further intermediate step of the exemplary embodiment of the manufacturing method is shown. While in the intermediate step explained with reference to FIG. 6B only the very top part of the constrained bristle tufts 220A will glide into the apertures, FIG. 6C shows the situation where the constraining structure 400 and the cover structure 100 are both moved in alignment into (coinciding) directions C3 and C2, respectively, such that the constrained bristle tufts 220A glide further into the apertures 110 until they will fully extend through the apertures 110 and the final spatial relationship between the cover structure 100 and the bristle carrier 200 is achieved, which is indicated in FIG. 6D. In the process of moving the constraining structure 400, the individual constraining elements may be moved first together downwards to the mounting surface 201 of the bristle carrier 200 in the direction C3 and then individually outwards (i.e. out of the way) until the constraining elements are moved to a position at which the final spatial relationship of cover structure 100 and bristle carrier 200 as shown in FIG. 6D can be achieved. In FIG. 6D it is further indicated that the bristle carrier 200 and the cover structure 100 may be mounted to each other by at least a mounting element 230A and/or 231A, in particular so as to enable relative movement between the cover structure 100 and the bristle carrier 200 as was already explained with reference to the exemplary embodiment shown in FIG. 2.

The brush head that is finally realized has the following structural features: a cover structure having at least an aperture and a bristle carrier to which at least a bristle tuft is mounted, the bristle tuft extending through the aperture, wherein the aperture has at least a first spatial aperture extension direction that is smaller than the respective width of the bristle tuft at its free end (where the width of the bristle tuft at its free end is in particular measured prior to the mounting procedure, as the finally mounted cover structure may to some extend still also constrain the bristle tuft as the constraining structure itself).

FIG. 7 shows an exemplary toothbrush 1 (here: an electric toothbrush) that has a brush head 10 manufactured in accordance with the proposed manufacturing method, which brush head 20 is disposed at an upper end of a handle 2 (here: the brush head 10 is arranged so as to be detachable).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing a brush head comprising the steps of:
    providing a bristle carrier on which at least a bristle tuft including a plurality of bristles is mounted;
    providing a cover structure having at least an aperture;
    constraining the free ends of the plurality of bristles of the bristle tuft into a defined cross sectional geometry such that it fits within the cross sectional area of the aperture;
    moving the cover structure and the bristle carrier relative to each other until the constrained bristle tuft and the aperture are positioned in spatial alignment; and
    releasing the constraint while moving the cover structure into a destination position in which the bristle tuft extends through the aperture.

2. The method of manufacturing according to claim 1, wherein the step of constraining the free ends of the bristles includes moving a constraining structure relative to the bristle carrier.

3. The method of manufacturing according to claim 2, wherein the constraining structure includes at least two constraining elements, wherein one constraining element is a comb-like constraining element having a plurality of prongs.

4. The method of manufacturing according to claim 3, wherein the prongs of the comb-like constraining element have rounded edges.

5. The method of manufacturing according to claim 3, wherein the constraining structure has four constraining elements forming two sub-constraining structures, each sub-constraining structure having two of the constraining elements, and the two sub-constraining structures being angled to each other.

6. The method of manufacturing according to claim 2, wherein in the step of constraining the free ends of the bristles, the constraining structure is moved from a first position close to the mounting surface of the bristle carrier to a second position close to the free ends of the bristles.

7. The method of manufacturing according to claim 6, wherein in the step of releasing the constraint the constraining structure is moved to a third position distal to the bristle carrier.

8. The method of manufacturing according to claim 1, further comprising at least two bristle tufts each have a plurality of bristles mounted on the bristle carrier.

9. The method of manufacturing according to claim 8, wherein at least four bristle tufts are mounted on the bristle carrier in at least two rows, each row having at least two tufts.

10. The method of manufacturing according to claim 8, wherein in the step of moving the cover structure into the destination position at least two bristle tufts move into the aperture.

11. The method of manufacturing according to claim 1, wherein the cover structure has at least two apertures.

12. The method of manufacturing according claim 1, wherein the step of constraining the free ends of the bristles of the bristle tuft includes compressing the bristle tuft such that the bristle density in the constrained part of the bristle tuft is higher than the bristle density of the unconstrained bristle tuft at the mounting surface.

\* \* \* \* \*